US006614532B1

United States Patent
Power et al.

(10) Patent No.: US 6,614,532 B1
(45) Date of Patent: Sep. 2, 2003

(54) APPARATUS AND METHOD FOR LIGHT PROFILE MICROSCOPY

(75) Inventors: Joan F. Power, Montreal (CA); Shao-wei Fu, Montreal (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/560,893

(22) Filed: Apr. 28, 2000

(51) Int. Cl.$^7$ .......................... G01N 21/00; G01B 11/28

(52) U.S. Cl. ....................................... 356/432; 356/630

(58) Field of Search ................................ 356/432, 630, 356/369

(56) References Cited

U.S. PATENT DOCUMENTS

| | | | | |
|---|---|---|---|---|
| 4,521,118 A | * | 6/1985 | Rosencwaig .................. | 374/5 |
| 4,522,510 A | * | 6/1985 | Rosencwaig et al. .......... | 374/7 |
| 5,272,342 A | * | 12/1993 | Kotani ..................... | 250/341.4 |
| 6,151,119 A | * | 11/2000 | Campion et al. ........... | 356/630 |

OTHER PUBLICATIONS

Polymer Science USSR vol. 27, No. 5, 1985, "The Spatial Distribution of Products of Photodegradation of Polyvinyl Chloride Under Intense Polychromatic Irradiation" by A.P. Aleksandrov, V.N. Genkin and V.V. Sokolov, pp. 1060–1065.
Journal of Applied Polymer Science, vol. 48, 1993, "Influence of the Experimental Conditions on the Photooxidation of Poly(vinyl chloride)" by J.L. Gardette, S. Gaumet and J.L.Philippart, pp. 1885–1895.
J. Applied Phys. 76, 1994, "Regularization Techniques Applied to Depth Profiling with Photoacoustic Spectroscopy" by R.J.W. Hodgson, pp. 7524–7529.
Applied Spectroscopy, vol. 50, No. 8, 1996, "Depth Profiling of Stratified Layers Using Variable–Angle ATR" by Robert A. Shick, Jack L. Koenig and Hatsuo Ishida, pp. 1082–1088.
J. Opt. Soc. Am, vol. 4, No. 1, 1987, "Optical Microscope Tomography" by S. Kawata, O. Nakamura and S Minami, pp. 292–297.

(List continued on next page.)

*Primary Examiner*—Zandra V Smith
(74) *Attorney, Agent, or Firm*—Ogilvy Renault; James Anglehart (57) ABSTRACT

The present invention comprises an apparatus and a method of microscopy, for measuring depth dependent profiles of optical absorption, photoluminescence and light scattering in thin films on length scales of a few micrometers to a several millimeters. The principles of this invention are also directly extendable to imaging absorption and scattering at other wavelengths, and the scattering of electrons, and neutrons in thin films on the same or shorter length scales. In the optical range, this depth profile information is recovered by the direct recording of micrometer scale images of a light beam propagating along the depth axis of the material under study. The recording is implemented using a crossed beam microscope apparatus in which a collimated optical beam from a light source is propagated through the material under test. An image is recorded along a view axis, oriented at 90 degrees to the source beam axis, through a cross sectional image transfer surface of the sample, so prepared as to allow transmission of light emitted from the irradiated region of the sample. This emitted light is used to transfer an image to a camera of the source beam propagating though the sample, through a microscope or optical system aligned along the view axis. The depth profile recovered by such a microscope has a composite depth variation, which may be mathematically described by the product of a profile of light attenuation with depth of the source beam in the sample, multiplied by a matrix contrast arising from a depth variation in light emission efficiency of the sample. A modified two beam configuration of the microscope permits the extraction of the light attenuation profile of the source beam in the sample, independently of the matrix contrast.

12 Claims, 4 Drawing Sheets

OTHER PUBLICATIONS

Anal. Chem. vol. 57, No. 7, 1985, "Theory of Spectroscopic Sampling in Thin Amorphous Films" by Paul W. Bohn, pp. 1203–1208.

Academic Press, London, 1984, Theory and Practice of Scanning Optical Microscopy, Chapter 5, "Applications of Depth Discrimination" by T. Wilson and C. Sheppard, pp. 123–139.

Optics Letters, vol. 24, No. 4. Feb. 15, 1999, "Microscopic Fluorescence Imaging of Bulk Defect Clusters in $KH_2PO_4$ Crystals" by S.G. Demos, M. Staggs, M. Yan, H.B. Radousky and J.J. De Yoreo, pp. 268–170.

Applied Optics, vol. 38, No. 1, Jan. 1, 1999, "Spatial Distribution of Two-Photon-Excited Fluorescence in Scattering Media" by Jinpin Ying, Feng Liu and R.R. Alfano, pp. 224–229.

Applied Spectroscopy, vol. 53, No. 12, 1999, "Longitudinal Light Profile Microscopy: A New Method for Seeing Below the Surfaces of Thin-Film Materials" by J.F. Power and S.W. Fu, pp. 1507–1519.

* cited by examiner

APPARATUS AND METHOD FOR LIGHT PROFILE MICROSCOPY

FIELD OF THE INVENTION

The present invention relates to a technique of depth dependent analysis in thin films using optical or other radiation, on depth scales of ca. 1 to several thousand micrometers.

BACKGROUND OF THE INVENTION

The capacity to reliably analyze and to recover images of the depth dependent properties of a thin film, which the invention specified in this application discloses, is of fundamental importance to both industrial film processing, materials science and to medicine.

Many processes employed in the fabrication of thin films for industrial applications involve or produce a depth variation of the material composition on the length scale of a few micrometers to a few millimeters. Many of the present day coatings systems used by industry consist of four or five layers or more, for example. The migration of additives such as plasticizers and stabilizers, through thin films is a commonly encountered problem, as is the problem of thermal and optical degradation, which directly affect film performance and lifetime.

In histology, the depth variation of tissue properties on micrometer length scales may be fundamental in understanding tissue function, assessing drug delivery, or in diagnosing disease.

While the problem of analyzing material composition with depth on these length scales is of great interest to a number of fields, relatively few methods exist to achieve this analysis both easily and reliably. This is true regardless of whether or not the analysis method is destructive of the material under study.

Past destructive depth dependent analysis methods for films have involved lateral (orthogonal to the depth axis) stripping or microtomy of thin layers from the original test material followed by chemical or optical analysis of the sampled layers. See the article by A. P. Aleksandrov, V. N. Genkin and V. V. Sokolov, Polym. Sci. USSR 27, 1188 (1985).

Primary difficulties with the above destructive sampling methods are the time and labor required by the stripping or microtomy procedure. The depth sampling is not always reliable: it is not always possible to ensure that layers of precisely equal thickness have been sampled, leading to calibration difficulties in expressing material composition as a function of depth. A strict conformity of the sample to a solely one dimensional (depth) variation of properties must usually apply. The number of depth samples that can be recovered by these methods is usually relatively small. Finally, the microsampling procedure itself may modify the sample itself or contribute depth dependent contamination of the sampled material.

A common destructive analytical method described in the article by J. L. Gardette, S. Gaumet, and J. L. Phillippart, J. Appl. Polym. Sci. 48, 1885 (1993) is associated with conventional light microscopy, and has been used for the depth analysis of polymeric materials. This latter preparation procedure involves embedding the test material in a matrix of resin which acts as a substrate for the cutting of thin cross-sectional slices (orthogonal to the depth axis) of said material, using a microtome apparatus. The thin cross-sectional slices which are cut from the material are then analyzed by transmission or reflectance microscopy.

The difficulties encountered with this procedure are numerous. The primary setting of the sample in the matrix is time consuming, and the, use of a microtome apparatus, while routine in many laboratories, is an expensive requirement of the sample preparation procedure. Many materials have weak adhesion to the resin substrate in which the test material is embedded. Individual layers comprising the material tend to easily delaminate under slicing by the microtome blade. This produces an obvious violation of the mechanical integrity of the original sample, and may seriously complicate the interpretation of the experimental micrographs.

As a result of the above complications, there may be many practical situations in which a destructive depth resolved analysis of a test material on the 1–100 micrometer length scale is not possible.

The above difficulties with destructive sampling methods have led to the more recent development of non-destructive methods of depth profile analysis, usually based on the interaction of optical radiation with the test material. An effectively comprehensive list of these methods consists of the following methods: (i) photoacoustic and photothermal spectroscopy (see the article by R. J. W. Hodgson, J. Appl. Phys. 76, 7524 (1994)); (ii) attenuated total reflectance (ATR) (see the article by R. Shick, J. L. Koenig, and H. Ishida, App. Spec. 50, 1082 (1996)) and variable angle reflectance methods; (iii) optical computed tomography (see the article by S. Kawata, O. Nakamura and S. Minami, J. Opt. Soc. Am. A 4. 292 (1987)); (iv) methods which integrate the material under analysis into the cladding of an optical waveguide (see the article by P. W. Bohn, Anal. Chem. 57, 1203 (1985)); and (v) techniques of confocal microscopy (see the article by T. Wilson and C. Sheppard, *Theory and Practice of Scanning Optical Microscopy*, Academic Press, London, 1984).

With the exception of confocal microscopy (as discussed in more detail below), the above methods are based on indirect depth detection mechanisms. In these cases, the experimental detector response is measured as a function of some depth sensitive parameter or condition in the experiment, and a depth profile of the sample properties is then recovered from a mathematical analysis of the detector data. The mathematical problem of reconstructing a depth profile of the sample properties from the experimental data in most of these cases, requires application of an inverse scattering theory. The reconstruction problem is usually very ill posed, which means that the experimentally measured signals have only a weak dependence on the depth of an optically interacting feature. In practical terms, ill posedness requires that the data being analyzed must be highly free of both systematic and random errors if the reconstructed depth profile is to be reliable.

For example, optical depth profiling methods based on photoacoustic and photothermal spectroscopy measure signals arising from transient or modulated heat flow in the test material. This heat flow in turn arises from light absorption as a function of depth in the sample, caused by irradiation of the sample with a pulsed or modulated optical beam. The measured photothermal or photoacoustic signal derives its depth sensitivity from the signal's dependence on the optical beam's modulation frequency (or, in the case of pulsed irradiation, on the delay time past application of a short irradiating impulse). This signal dependence is mathematically related to the depth of an absorbing feature below the surface. Reconstruction of a depth profile of optical absorption from photoacoustic or photothermal signals has been experimentally demonstrated, but to date, this can only be done if the sample is substantially planar, having a variation in structure along the thinnest dimension, which are called herein the depth dimension, and substantial homogeneity along all directions transverse thereto. Materials for optical photoacoustic or photothermal depth profile analysis must furthermore be substantially homogeneous in their thermal properties, and measurements must be carried out under conditions of a precise knowledge of the sample's detection geometry. Relative errors in the experimental data must be less than 1% of the full scale signal, typically, for a reliable depth profile reconstruction.

A related set of depth profiling techniques based on attenuated total reflectance (ATR) of an optical beam, measure depth dependent optical absorption in the test material by launching evanescent optical waves into the material. This is accomplished by means of a slab or guide of optical material of large refractive index which is physically contacted to the material under test. By varying the launch angle of radiation entering the slab, the depth of penetration of the evanescent wave into the test material is varied, ultimately causing a variation in the radiation intensity leaving the slab. A mathematical relationship has been derived between the absorption depth profile of an arbitrarily layered planar material and the launch angle dependence of the radiation intensity transmitted by the optical slab or guide. Mathematical procedures, based on inverse scattering theory, for recovering a depth profile of optical absorption from the experimental data have also been published. However, this depth profiling method has many problems in common with the photoacoustic photothermal depth profiling method described above, including the requirement for high quality experimental data and a precise control of all experimental errors. The sample geometry must be carefully controlled and data of very high precision must be available to obtain a meaningful depth profile. Finally, the optimum performance for this method is restricted to a depth range of less than ten micrometers, which is not convenient for many practical problems.

A class of depth profiling methods related to those based on ATR, use integration of the test material into the cladding of a planar optical waveguide. By varying the launch angle of an optical beam into the waveguide, individual waveguide modes of varying order (index) are excited. These mode fields penetrate the cladding (which the test material comprises) to a variable extent depending on the mode field index. The cladding material may luminesce, absorb or scatter the excitation light, and will do so to a depth variable extent depending on the spatial distribution of the electric field excited in the guide for a particular waveguide mode. A known mathematical relationship exists between the mode field index and emission depth profiles of arbitrary dependencies for planar structures, but like the ATR problem, this method is extremely ill posed and highly indirect. It requires even more stringent controls on experimental conditions to recover a reliable depth profile from the test material.

More recent optical depth profiling methods have been advanced based on optical computed tomography (OCT). This method involves optical irradiation of the sample from many directions with measurement of an image of the sample for each direction of irradiation. A volume distribution of optical absorption, scattering or photoluminescence may then be reconstructed mathematically from an optical model of the ray propagation (or diffraction) as a function of irradiation angle. This problem, as with methods (i)–(iv) above, is indirect, and ill posed, requiring the stable solution of an inverse scattering theory for reconstruction of the volume distribution.

Confocal microscopy is a more direct method for recovering depth dependent images of materials. This method derives its depth dependence from the precisely controlled conjugate relationship which is experimentally maintained in the microscope system, between the measured image and an individual slice plane of an irradiated depth dependent object. This relation strongly rejects out-of-focus light contributions in the image, which originate from object planes above or below a precisely defined conjugate plane of interest.

This method has a greater potential depth discrimination for images individually based on light absorption, photoluminescence and light scattering by the object. A one dimensional planar geometry is not required. However, this method is still indirect, and derives its depth dependence from an assumed value of the refractive Index of the sample. Depth position calibration of the measured images may be affected by refractive index gradients in the sample, both along the axis of the microscope and transverse to it. This may prove to be a serious disadvantage in the analysis of complex materials.

SUMMARY OF THE INVENTION

It is therefore an object of the invention to provide an improved method and apparatus for analyzing depth dependent properties of thin films, coatings or thin materials. The improved method and apparatus leads to a directly obtained image of radiation interaction as a function of layer depth without destructive sampling of the depth region of interest. The improved method and apparatus also exhibit reduced perturbation by the index of refraction.

According to one aspect of the invention, there is provided a method and apparatus for measuring depth dependent optical absorption, photoluminescence and light scattering in a sample with depth dependent optical properties. This method of depth profile measurement has a number of advantages over the prior art, which are discussed in detail below. These advantages consist of directness of the detection mechanism, simplicity of the apparatus and measurement principles, simplicity of sample preparation and ease of calibration of the length scales involved in the measurement. No mathematical processing of the image is required for direct qualitative inspection of absorbing and scattering features. In addition, this new method of optical measurement may provide several possible mechanisms of image contrast simultaneously, including some new contrast mechanisms. The prior art techniques usually implement one contrast mechanism at a time.

According to the invention, there is provided a method of analyzing composition or structure of a thin film or layer by measuring a depth dependent profile of at least one of absorption, photoluminescence, secondary chemiluminescence, black-body emission and scattering of radiation in the thin film or layer. The method comprises providing a suitable test material having a depth axis extending through a thin film or layer, the test material being provided with a substantially flat image transfer surface having an orientation substantially parallel to and in proximity to the depth axis, projecting a beam from a source of radiation into the test material along the depth axis thereby causing emission of radiation from the test through the image transfer surface; and collecting at least part of the emission of radiation transmitted through the image transfer surface to form an image of a depth dependent profile of at least a part of the thin film or layer.

According to another aspect of the invention, there is provided an apparatus for light profile microscopy comprising the following elements:

a radiation source which provides a collimated radiation beam;

a suitable test material through which the collimated radiation beam propagates along an axis called the depth axis, and in which test material, the collimated radiation beam irradiates the test material in the volume intersected by the collimated beam and the test material, the volume being called the irradiated volume of the test material, wherein radiation emission occurs from the irradiated volume of the test material by scattering or luminescence;

a substantially flat surface of the suitable test material, called the image transfer surface, the surface having orientation parallel to the depth axis, and through which the surface the radiation emission from the irradiated volume of the test material is transmitted;

a imaging system aligned with its principal axis oriented perpendicular to the image transfer surface, and also aligned so that the principal axis intersects the irradiated volume, the imaging system being aligned also so as to form an image of the irradiated volume from radiation emitted from the irradiated volume and transmitted through the image transfer surface of the test material;

a camera or image recording device which records the image formed by the imaging system.

BRIEF DESCRIPTION OF THE DRAWINGS

The invention will be better understood by way of the following detailed description of specific preferred embodiments with reference to the appended drawings, in which.

DETAILED DESCRIPTION OF THE PREFERRED EMBODIMENTS

In the following description, specific embodiments of the invention are described for the purposes of teaching and enabling the present invention. It will be appreciated that many of the features, components and steps described in connection with these embodiments are not essential to other embodiments of the same invention, which other embodiments have not been described herein for the sake of brevity.

Figure 1:
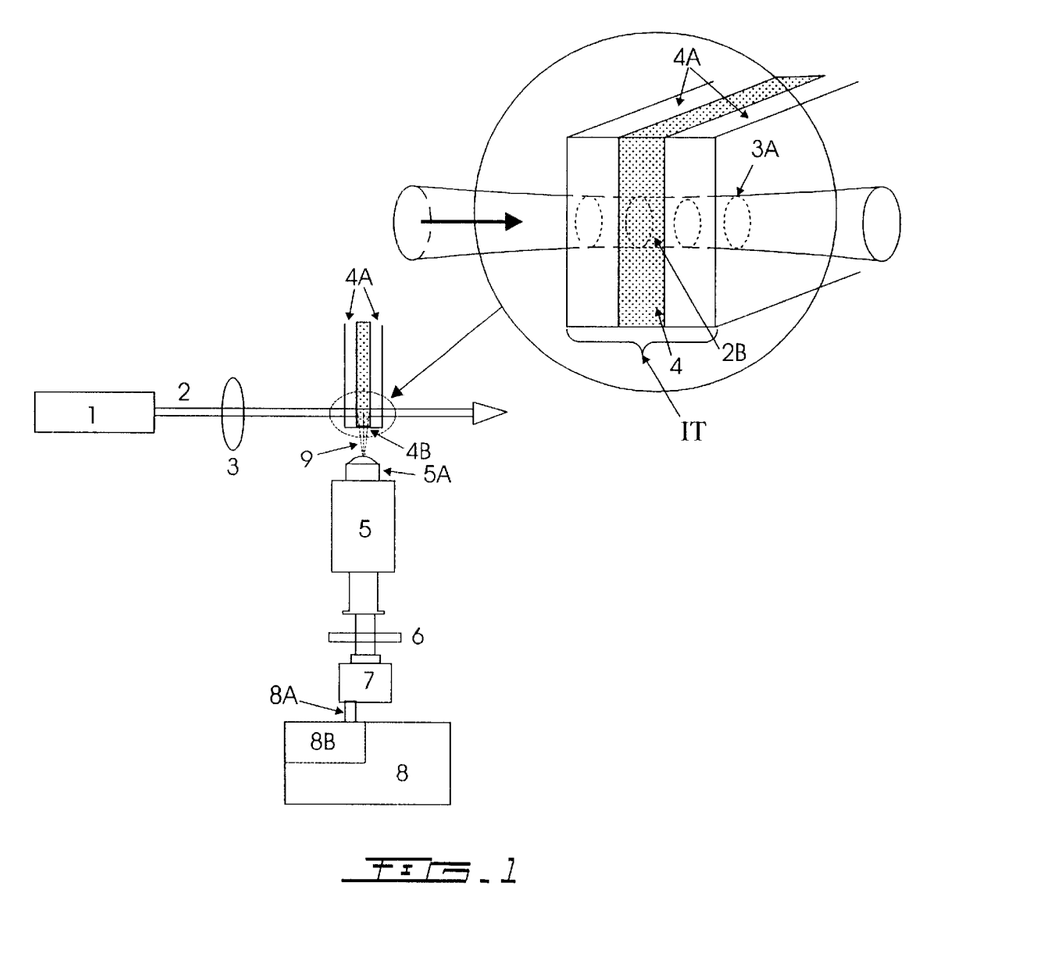
FIG. 1 is a schematic diagram of the first preferred embodiment using a single beam.

An apparatus embodying the principles of the present invention is diagramed in FIG. 1. This schematic shows the most general implementation of the principles of the apparatus of the invention. The apparatus uses a collimated beam (2) from an optical radiation source (1) which is propagated through a suitable test material (4) (inset). In the most widely applicable case, the suitable test material will be a thin film having a substantially planar structure planar, in which a variation in structure occurs along the thinnest dimension, called the depth dimension, and there is substantial material homogeneity along all directions transverse thereto. As a minimum, this requires that the test material have a locally planar structure in the sense that the average properties of the material do not systematically vary along directions perpendicular to the depth axis within a region less than 3 source beam diameters in any direction from the source beam axis. This structure accommodates the possible presence of spurious defects in the material producing a random variation of the material's depth properties from the average, however. The contribution of such defects may be seen as a measurement error, and suitable image sampling measurements may be invoked to minimize them. The source beam will be propagated along the film's depth axis. The suitable test material will also have depth dependent optical absorption and/or luminescence and/or light scattering on a microscopic to mesoscopic (about 1 $\mu$m to about 5–8 mm) length scale, although a depth invariance of optical properties is not excluded by the invention's principles. The source beam is normally aligned so as to propagate along the depth axis of the material. Attenuation of the source beam in the direction of the depth axis will occur if the sample absorbs or strongly scatters radiation at the irradiation wavelength.

In the volume of the test material which is irradiated by the source beam (2B), light is emitted according to several mechanisms. Commonly, light is scattered by elastic scattering mechanisms such as Rayleigh, Debye or Mie scattering. Photoluminescence and inelastic scatter may also occur depending on the material properties. Other possible emission processes accompanying light absorption in the material include black-body emission (in response to sample temperature changes), and secondary chemi-luminescence which may be initiated by photochemical changes in the material. The distribution of light intensity produced by these emission processes varies with composition along the depth axis of the test material.

The apparatus of the present invention uses light emitted according to the above processes from the irradiation volume of the test material, to form an image of the light intensity distribution present in the irradiation volume (2B). The light intensity distribution corresponds to a weighted image of the source beam profile propagating along the test material's depth axis, where local light emission efficiency variations caused by depth variations in composition may produce the depth weighting of the image of the source beam profile as it propagates through the test material.

The apparatus forms an image of the emission intensity distribution in the irradiation volume by means of an imaging system (elements 5A and 5) which is aligned to collect light emitted therefrom. Because of the length scale of the depth axis of most thin film test materials, the imaging system will usually be an optical microscope, although imaging systems of lower magnification may be appropriate for the inspection of samples of greater depth dimension, which the operating principles of the apparatus do not exclude.

Image formation by the imaging system (5,5A), of the light distribution in the test material's irradiation volume, requires that an image transfer (IT) surface be available through which light emitted in the test material's irradiation volume must pass before being collected by the imaging system. This IT surface must be oriented parallel to the depth axis: all normals to the IT surface must be oriented orthogonal to the depth axis. The IT surface must be located sufficiently close to the irradiation volume that optical transmission is high enough for detection of the image formed by the optical system. The IT surface must be substantially free of optical defects such as scratches and digs, so that no significant contributions therefrom appear in the image formed by the optical system. The IT surface should normally be substantially flat. The IT surface must be of an area sufficiently large that the entire irradiation volume, or a significant portion thereof, may be viewed by the imaging system. These conditions may be arranged by intersecting the test material with a source beam aligned parallel to an exposed cross sectional edge of the material, and by polishing the exposed edge to a surface finish of suitable optical quality. For example, the finish obtainable by lapping with a polishing surface having a surface finish of 3 μm or less is acceptable for low magnification measurements.

The imaging system is aligned along an imaging axis, which is oriented orthogonally to the IT surface, and aligned to intersect the sample's depth axis at or near its midpoint—which is the point located on the axis halfway between the surfaces of the test material. The object plane of the imaging system is set at a plane in the test material containing the central axis of the irradiation volume, which also coincides with the central axis of propagation of the source beam in the material. The image formed under these conditions is an image of the emitted light intensity distribution in a cross section of the irradiation volume, centered in a plane containing the source beam's central axis, and averaged along a thickness dimension, approximately equal to either the focus depth of the imaging system along the imaging axis, or the source beam's dimension also the axis, whichever quantity is smaller.

The image thus formed by the imaging system is detected by a camera or imaging device (7) located in a plane conjugate to the object plane of the microscope stage. The output signal from the camera or imaging device may be read out and digitized by an optional data converter and data storage/processing system such as a computer (elements 8,8A, 8B).

The detected image will have a variation in contrast along the depth axis of the test material, and also along an axis orthogonal to both to the depth axis and the imaging axis, which is called herein the vertical axis of the image.

The detected image is a weighted image of the source beam intensity distribution along the depth and vertical axes, and averaged along the focus depth of the microscope stage. Because it forms a weighted micrometer to millimeter scale image of the light profile of the source beam propagating along the depth axis of the test material, the apparatus of the invention is called a light profile microscope (LPM).

The advantages of this method of image detection may now be readily seen.

First, preparation of the sample is simple. Preparation steps normally involve the slicing, polishing and, optionally, finishing, of a IT surface in the test material by readily available means. If the test material is delicate, it may be embedded between supporting pieces of glass or polymer (elements 4A) for polishing. Sample preparation procedures for most thin film materials which are solid at room temperature require as little as an hour or less of preparation time, compared to prior art procedures requiring many hours to days, as well as the use of specialized equipment. Furthermore, unless the test material is unusually delicate, this method of sample preparation is minimally perturbative of the material structure.

Second, viewing of the image features by this method is direct. No other existing inspection method can obtain optical information about the sample as directly as with this apparatus. This provides a third advantage: the length scales and dimensions of all detected features viewed are easy to calibrate, and the locations of all detected interface structures and surfaces in the test material are unambiguous.

Fourth, the design of the apparatus is relatively simple and may be implemented using any well collimated optical beam, a sample mounting stage, a metrology microscope and a CCD camera. Alignment of the apparatus is simple and relatively robust to errors at moderate magnification levels.

Finally, optical inspection with this method offers the advantage of possible new mechanisms of image contrast in the depth profile, that have not been exploited in previously existing microscopes. The nature of the images detected by light profile microscopy have recently been analyzed theoretically by the inventors. The depth dependence of the light profile measured by a light profile microscope (LPM) has been shown to be describable by the following equation:

$$\delta I_z = I_0 \exp\left\{-\int_0^x \beta(u)\,du\right\} \cdot C(x) \tag{1}$$

where β is the depth dependent optical attenuation in the test material, $I_o$ is the light intensity incident on the material, and C(x) is a depth dependent image profile along the depth axis, x, called the matrix contrast, which arises from combined depth variations in light scattering and photoluminescence efficiency of the test material.

The image contrast arising from depth attenuation of the source beam is given by the integral factor in equation (1), $$I_0 \exp\left\{-\int_0^x \beta(u)\,du\right\},$$

which is called herein the attenuation contrast. This is a property of fundamental importance, because in many situations, specifically, the regime of weak scattering, it is dominated by the sample's depth profile of optical absorption. The optical absorption can be directly used to qualitatively, and sometimes quantitatively evaluate the composition of a material. Calibration and interpretation of the depth profile of optical absorption is usually much simpler than for photoluminescence contrast.

On the other hand, the matrix contrast C(x) arises from several underlying light emission mechanisms which are more difficult to calibrate. Some of these emission mechanisms, such as elastic light scattering, have highly enhanced sensitivity to interfaces and subtle differences in the particle morphology of materials. They have not been used in prior techniques of microscopy with the right angle viewing geometry introduced by the present invention, as this inspection geometry is new. These contrast mechanisms open up new possible new insights into the layered structure of materials.

Figure 2:
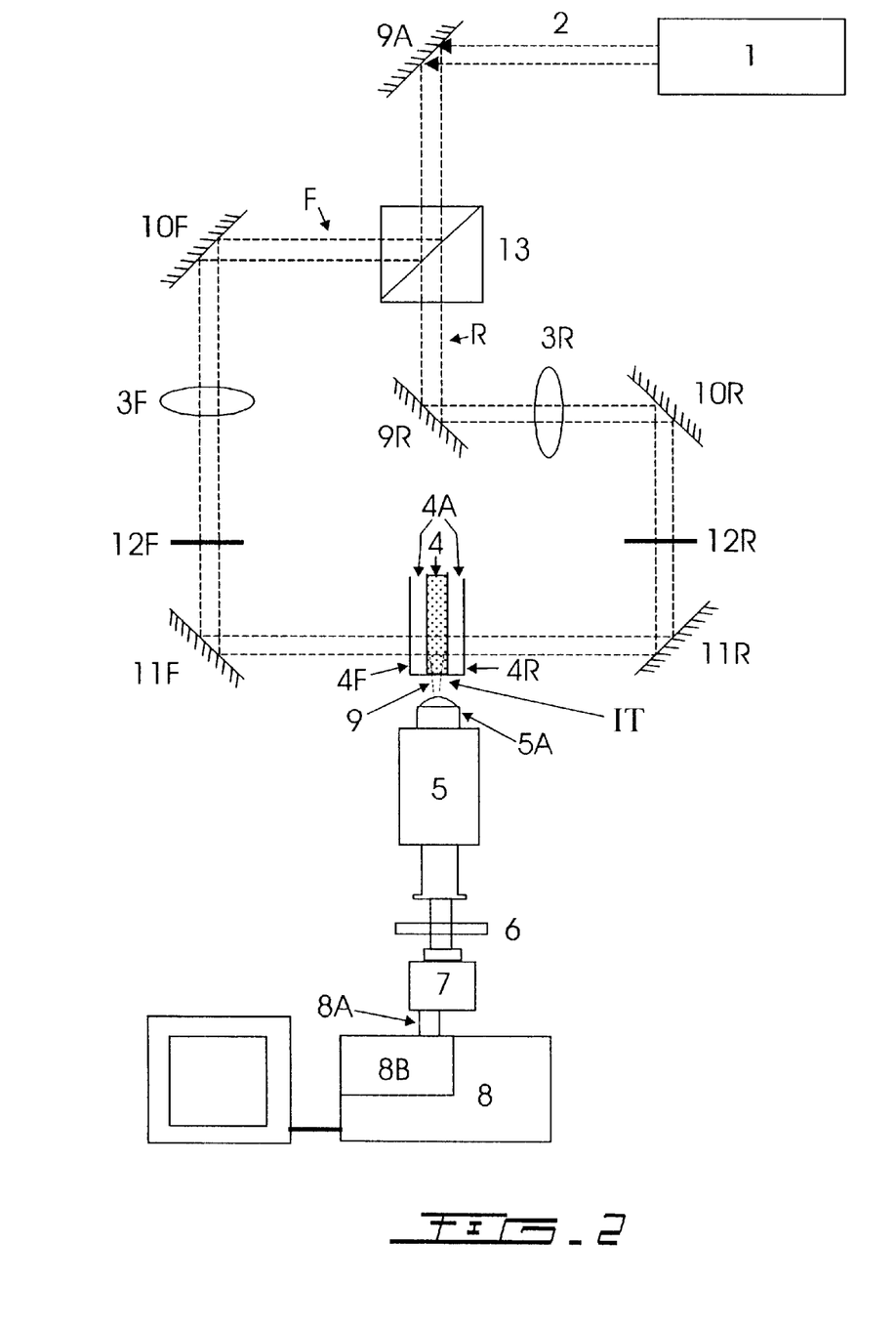
FIG. 2 is a schematic diagram of the second preferred embodiment using a pair of opposed beams.

Interpretation of the composite contributions to a light profile microscopy depth profile image is normally a complex problem. If the image contrast due to light absorption may be separately resolved from the matrix contrast, this constitutes an important simplification of the LPM image. Such a contrast separation may be achieved experimentally by a simple modification of the basic LPM apparatus presented in FIG. 1. FIG. 2 shows an apparatus modification of the basic light profile microscope, which may be used to experimentally resolve an LPM image due to light attenuation contrast, from an LPM image arising from matrix contrast. The configuration of the second apparatus has the important difference from the first apparatus that, instead of using a single collimated beam, two identical collimated beams (F and R) are generated from a source of radiation by means of a beam splitting element and associated beam collimation optics. A set of beam steering optical elements (9R,10F, 10R 11F and 11R) is used to direct the two beams through the test material along its depth axis from two precisely opposing directions. These two directions consist of a first forward direction, and its opposing reverse direction. The source beam paths (F and R) are intersected by shutters (12F and 12R) which provide consecutive and individual transmission of the forward and reverse directed beams through the test material along its depth axis. With exposure of the test material to each of the forward and reverse beam, an irradiation volume is established in each exposure by means of irradiation towards the respective forward (4A) and reverse (4R) surfaces of the test material (4). A imaging system (Elements 5A and 5) is used to form an image of the irradiation volume established from each of the directions and a camera (7) is used to record each of the images. A data acquisition and processing system (Elements 8,8A and 8B) is used to store the image data recorded by the camera and to provide mathematical processing of the forward and reverse images.

The data recording and processing system (8,8A,8B), was optional in the first configuration, but is important in the second configuration (FIG. 2) of the apparatus. This is so because a further stage of mathematical processing must be performed on the forward and reverse images recorded by the second apparatus in order to separately resolve an, image arising from the attenuation depth profile contrast from that arising from matrix contrast, C(x). The separation of contrast mechanisms is based on the principle that the two opposing beams sample identical depth coordinates through the sample. Light attenuation of the image profile due to absorption or strong scattering will vary with the direction of beam propagation while any profile variation along 'x' caused by the matrix contrast will be identical regardless of the direction of illumination for the same irradiated coordinates. A mathematical model can be used to fit a depth profile of the optical attenuation, which in preferred cases will be dominated by the optical absorption coefficient of the sample at the source beam wavelength. This is performed by the computer system using appropriate software.

It should be emphasized that the usual condition for which the embodiment of FIG. 2 applies to recover the depth dependence of the optical absorption coefficient from the matrix contrast C(x), will be under conditions of weak light scattering from the sample: the so called nephelometric regime. Under this condition, the attenuation contrast in Eqn. (1) is dominated strongly by optical absorption. On the other hand, if light scattering becomes strong, the attenuation contrast arises from the joint effects of optical absorption and scattering. This joint information is more difficult to interpret, and therefore the operation of the microscope under this condition yields information which is less well defined. However, such information is not useless, and operation of the embodiment of FIG. 2 remains applicable with strongly scattering samples.

At this point a number of possible arrangements (and constraints) of specific physical elements are addressed which will satisfy the principles embodied by the apparatuses of FIGS. 1 and 2.

The requirement for a substantial collimation of the excitation beam is based on the following considerations. First, it is desired to limit the spatial extent of the source beam along the microscope's optic axis, 'z', so that the degree of defocus along 'z' does not vary significantly with the depth 'x'. The degree of defocus along 'z' is directly controlled by varying the radius of the collimated beam irradiating the sample. The use of a non-collimated beam degrades thus degrades resolution in the depth variable 'x'.

A second consideration is that if absorption and emission from the test material are to be faithfully recorded as a function of depth, the source beam rays should pass through the sample in straight lines parallel to the depth axis. If a non-collimated source beam is used, individual ray trajectories are no longer maintained parallel to the depth axis, and the recorded images are no longer unambiguously interpretable in terms of the depth properties of absorption and/or emission.

In the absence of collimation, therefore, the resulting image suffers from degraded spatial resolution, and ambiguous depth dependence. However, if the material is substantially planar, some depth information such as the position of vertical interfaces may still possibly be recovered.

Finally, if the collimated source beam propagating through the test material encounters regions of the material with a substantial variation of optical properties such as transmission, refraction or reflection across the source beam diameter, then the beam's ray trajectories may be substantially disrupted from the preferred condition of parallelism to the depth axis. This amounts to a substantial departure of the required planarity of the sample, as discussed above. The images resulting from this analysis can no longer be properly interpreted as light profile images.

The ninety degree angle to be established between the source beam in the test material and the optic axis of the imaging system, is strongly preferred because it is normally desired to image the light profile along the depth axis in its entirety (or a substantial fraction thereof) with all image elements detected simultaneously. Viewing from angles significantly different from 90° would produce refractive distortion of the image requiring mathematical correction. Even if scanning of the image formed by the imaging system were used (which the apparatus does not exclude) the 90° geometry provides the most direct and unambiguous view of the light profile illuminating the material. The amount of tolerance on the orthogonality, is of the order of a few degrees for low magnification microscope stages. This tolerance is smaller as the field and magnification of the imaging system increase.

The IT surface must be substantially flat over the aperture and field covered by the microscope stage for two reasons. First, a substantially non-flat IT surface may introduce a significant variation of the object distance (from the microscope stage) over the surface. This results in the introduction of aberrations (with possible distortion) into the image. It is therefore infeasible to view the irradiation volume through a significantly inclined IT surface (>5° of inclination for low magnification microscope stages) or an IT surface which is substantially curved, unless some form of optical compensation is introduced. Such corhpensation would require a knowledge of the refractive index and optical dispersion of the test material, which would be impractical, in general, for an unknown material. It is also understood that the test material has a depth variation of refractive idex at the image wavelength which is small in the sense that no significant variation in the object distance of the microscope is produced across the object field.

Second, the IT surface must be flat in the sense of being free of scratches, digs and other optical defects, so that no contributions of scattering or diffraction therefrom may appear substantially in the detected image. Under the usual conditions, the IT surface is displaced outside of the focus depth of the microscope stage, so that such contributions from surface flaws are strongly out of focus and therefore do not appear in the detected image. However, In some situations it may be desirable to inspect a region of the material which is close to the IT surface. The closer the positioning of the irradiation volume to the IT surface, the finer the surface finish must be. For general purposes, with a low magnification microscope stage and a distance of 0.1–0.5 mm of the irradiation volume center from the. IT surface, in a material of refractive index 1.33, a surface finish of 0.5–3 $\mu$m or less is acceptable.

The radiation source used to supply the source beam is most typically a laser, because laser sources readily provide highly collimated beams at high radiance. Broadband optical sources may only be used provided they are equipped with collimation optics having a large F number and can produce sufficient irradiation power, that the image can be, detected. These specifications may not preclude the use of a broadband optical source of sufficiently high radiance equipped with an interferometer having a sufficiently large throughput and large F number optics.

A light profile microscope in the most usual configuration is a optical device operating in the wavelength range of 200 nm–50 micrometers. Other wavelength ranges are not excluded by the apparatus provided a compatible imaging and detection system is available. A collimated X-ray source of suitable intensity and collimation may be admissible to supply the source beam. Both x-ray fluorescence and scattering may then provide suitable contrast. The use of electron, neutron or other particle beams is also possible to supply the source beam, if such beams can be collimated to a high degree without loss of intensity.

The imaging system used by the apparatus of the present invention to form an image of the irradiation volume or volumes established in a test material, is considered in this specification to be a device which forms a magnified image of a small object suitable for recording by a camera or image recording device. However, situations may arise in which the camera aperture could be smaller than the dimensions of the irradiation volume viewed. In those cases, an imaging system with a magnification of unity or less would be admissible.

Many different types of imaging systems are potentially compatible with the embodiment of a light profile microscope. An optical transmission microscope operating in the visible-near IR is the most typical microscope stage that can be used in the wavelength range of 350–1000 nm, as is such a microscope equipped with quartz optics for ultraviolet imaging over the range of 200 nm–350 nm. An infrared microscope or imaging system may be used over the range of 1–50 $\mu$m. Such microscope stages may be of the classic broadfield (parallel imaging) design, or alternatively a scanning microscope stage may be used. The use of a confocal microscope of either the scanning or broadfield design is also admissible, and has the useful capability of imaging a very thin plane in the irradiation volume. Although, in most applications, the test material under study would have a substantially planar (or parallelepiped) structure (with slow or negligible variation of detected film properties along the imaging axis of the microscope), the use of a confocal microscope stage for image formation would allow the imaging of samples with a substantial variation of composition along the microscope's imaging axis to be recovered.

A microscope stage or imaging system composed of electron or ion imaging optics, used in conjunction with an electron or ion source is not excluded. This microscope stage may also be either of the scanning or broadfield type.

In the simplest case, where a mathematical analysis of the image data is not desired, the camera or imaging device used by the apparatus may be a conventional camera equipped with a photographic plate. In the most general case, however, the camera will be a device operating over the range from the near ultraviolet to the near infrared, based on charged coupled device (CCD) technology, interfaced to a computer based storage and data processing system. Other compatible devices include solid state infrared cameras, and the combination of a silicon intensified target with a visible wavelength camera. If the microscope stage is a scanned device, applicable point imaging detectors include a single photodiode (for a scanned confocal microscope stage) and a single channel electron multiplier tube (for a scanning electron microscope stage).

Because the emission mechanisms used by an LPM include fluorescence, phosphorescence and Raman scattering, the emission wavelength dependence of these processes may be exploited, in some cases, to determine chemical composition or physical matrix properties of the test material with depth. The introduction of a wavelength dispersing device may be used to permit image recording at multiple individually resolved emission wavelengths. At fixed image position, a spectrum of the light emitted from of the material's irradiation volume is recovered from the multiple images recovered as a function of wavelength. A depth mapping of the composition and/or physical structure may thus be made. In low wavelength resolution measurements, the wavelength dispersing device may be a broadband color filter. For high resolution spectral imaging, the color filter would be replaced by an imaging spectrograph, and acousto-optic or an electro-optic tunable filter.

Individual Embodiments used for Scattering, Absorption, Photoluminescence and Raman Contrast Image Measurements FIG. 1 shows the simplest.practical embodiment of the apparatus as it would be used for a single beam imaging measurement A source beam (2) is obtained from a laser (1) and focused through a lens (3) which forms a collimated laser beam waist (3A) in the test material (4), where the Rayleigh range of the source beam waist is larger than the thickness dimension of the test material, to ensure acceptable collimation of the beam in the material. The test material (4) is supported between rigid slabs (4A) of a material which is transparent at the source beam wavelength. The irradiation volume (2B) established by the source beam in the test material emits light (9) which is transmitted through the IT surface and collected by a microscope objective (5A). The microscope objective is focused so that its object plane is centered on the irradiation volume (2B). An image of the intensity distribution of light in the center of the irradiation volume is formed by the microscope (5). The microscope image is focused onto a camera or imaging device (7) and the electronic output of the camera is transmitted by a cable (8A) and into a computer (8), which is equipped with data conversion and sampling circuits (8B) which convert the camera image signal into a digital format, which is stored in the computer for possible future analysis.

An optical wavelength selecting filter (6) may be used to select a wavelength range of interest to enhance a desired image contrast, such as photoluminescence, Raman scatter or elastic scatter, in the irradiation volume.

FIG. 2 shows an embodiment of the apparatus using the double beam configuration which is useful for separating light attenuation contrast in the recorded image from matrix contrast. A source beam (2) is obtained from a laser (1). The source beam (2) is directed by a mirror (9A) to a beamsplitter element (13) which splits the beam (2) into two paths (F) and (R). The beam following the path (F) is called the forward beam. The forward beam is directed to a mirror (10F), through lens (3F), downstream of which it encounters a shutter (12F), followed by a second mirror (11F). The lens (3F) forms a laser beam waist in the test material, with a Rayleigh range large enough to ensure good collimation in the test material (4). The test material is supported between slabs of a rigid material (4A) which is transparent at the source beam wavelength. The forward beam enters the test material through the material's front surface (4F).

Downstream of the beamsplitter (13), the beam following the path (R), is called the reverse beam. The reverse beam is reflected by mirror 9R, directed through focusing lens (3R), and then reflected at mirror (10R). Downstream of (10R), the reverse beam encounters a shutter (12R) which is held closed when the forward shutter (12F) is held open and vice versa. Downstream of mirror (11R) at which the reverse beam is reflected, a waist of the reverse beam forms in the test material (4), entering the material by the rear surface (4R).

An irradiation volume is consecutively established in the test material by means of irradiation from the forward beam or the reverse beam, as the shutters (12R) and (12F) are alternately opened and closed. Emitted light (9) from the irradiation volume is thus established consecutively by irradiation form the forward and reverse direction. It is desirable but not essential that the irradiation volumes established by forward and reverse beams occupy an identical set of spatial coordinates. If these coordinates are identical, the possibility of errors in measurement of the average depth properties of the material is minimized: such errors may arise from the presence of spurious defects in the material which depart randomly from the average depth variation of properties. The emitted light (9) is collected by the microscope objective (5A), and the remaining elements (5,6,7,8A,8B, and 8) function identically to the correspondingly numbered elements in FIG. 1, for consecutive measurements of the images recorded with forward and reverse irradiation. Mathematical processing is then applied to the consecutively recorded images, to recover an image of the test material which is dominated by absorption contrast, independently of contributions of the sample's matrix contrast.

Figure 3:
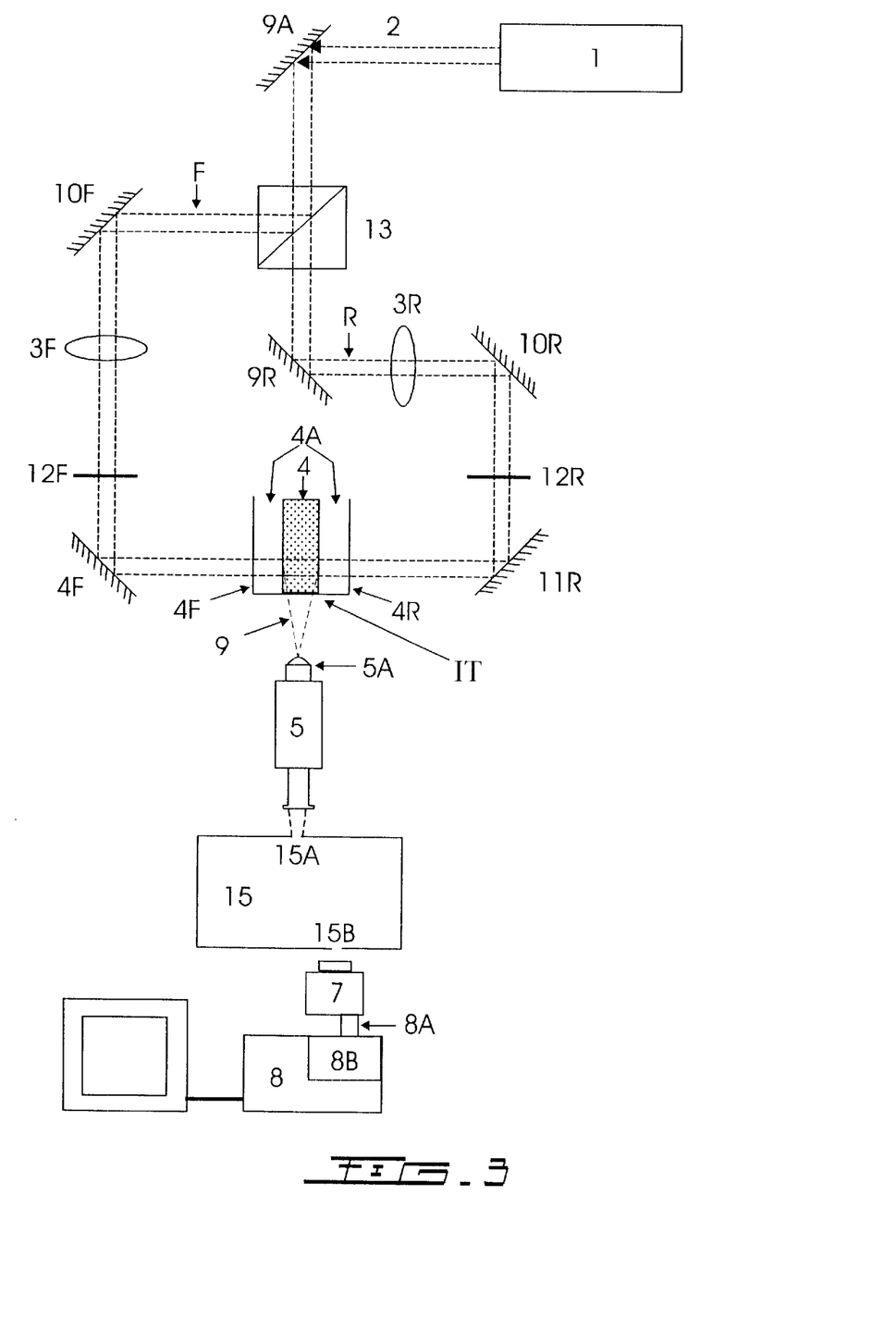
FIG. 3 is a schematic diagram of the third preferred embodiment using a pair of opposed beams in which the detector includes a spectrogram device.

The embodiment diagramed in FIG. 3 is used to recover wavelength dependent Raman scattering images of a test medium. The wavelength of the Raman scattered light may be very close to the excitation wavelength (at which elastic scattering occurs). A means of separating the images formed at closely spaced wavelengths is provided by means of a high resolution monochromator (15) which is integrated into the embodiment.

Figure 4:
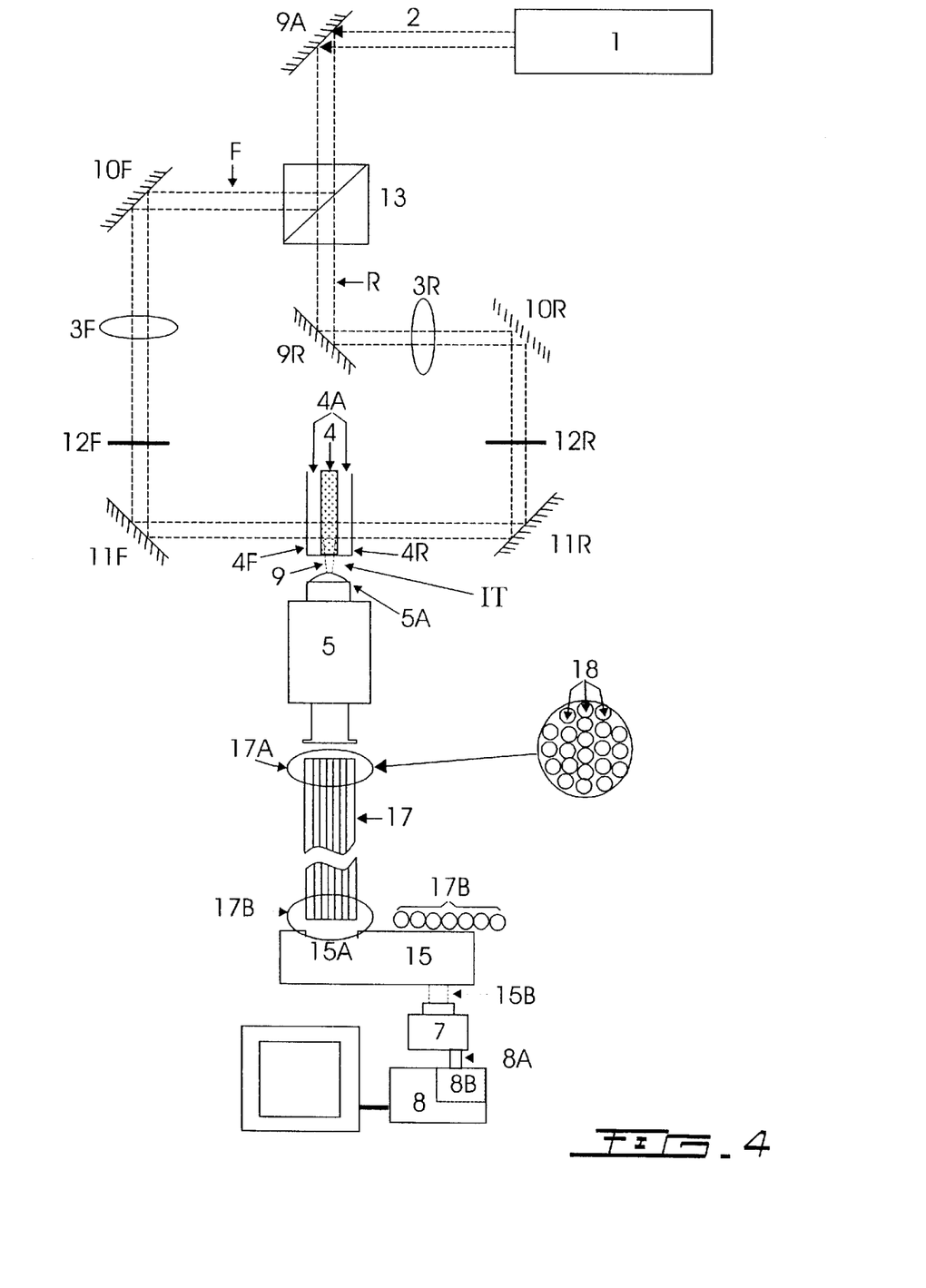
FIG. 4 is a schematic diagram of the third preferred embodiment using a pair of opposed beams in which the detector includes a spectrogram device and the image collected by the imaging optics is relayed to a fiber optic bundle arranged to convert the image into a linear array of fiber output beams for spectrogram analysis.

The embodiment of FIG. 3 contains Element Nos. (1,2, F,R,3R,3F,4,4A,4F, 4R,5A,5,9,9A,9R,10F,10R,11F,11R, 12F,12R,13) as well as elements (7,8,8A and 8B) which function identically to the counterpart elements of the same number in FIG. 2. However, in FIG. 3, an imaging spectrograph(15) is inserted between the microscope (5) and the recording camera (7) to permit the observation of wavelength resolved images at the output focal plane of the spectrograph (15B). It is assumed that the spectrograph maintains a conjugate (object/image) relationship between the entrance slit plane (15A) and the output focal (15B) plans, and that the spectrograph is well corrected for optical aberrations. The image from the microscope (5) is formed at the entrance slit plane (15A) of the spectrograph and transferred to the output focal plane of the spectrograph (15B). Another possible embodiment for Raman effect imaging, shown in FIG. 4. In this figure, Element nos. (1, 2, F, R. 3R, 3F, 4, 4A, 4F, 4R, 5A, 5, 9, 9A, 9R, 10F, 10 11F, 11R, 12F, 12R, 13) as well as elements (7, 8, 8A and 8B) function identically to their identically numbered counterparts in FIG. 2. The embodiment of FIG. 4 involves insertion of a fiber optic bundle (17) between the microscope (5) and the imaging monochromator (15). The image from the microscope is focused onto the input end of the bundle (17A) where the individual fibers (18) are aligned in parallel in a circular bundled configuration. The individual fibers in the bundle (18) are realigned on the output end (17B) into a linear array (inset) at the entrance slit (15A) of the imaging spectrograph (15). Light emerging from such a line array is easily transferred through the spectrograph (15) to produce a set of wavelength resolved images of the line array in the spectrograph's output focal plane (15B). A charge coupled device (CCD) based camera (7) detects a series of wavelength separated images of the line array of optical fibers as formed by the imaging spectrograph(15) in its output focal plane (15B). The output of the camera (7) is read into the memory of a computer (8) via an interface cable (8A) and a on-board data acquisition and conversion system (8B). The data from the line array images recorded by the camera (7) are then processed and re-mapped to a two dimensional image format using computer software.

The present invention is further described in Applicants' paper entitled "Longitudinal Light Profile Microscopy: A New Method for Seeing Below the Surfaces of Thin-Film Materials", published in Applied Spectroscopy Vol. 53, Number 12, 1999, the disclosure of which is hereby incorporated by reference.

We claim:

1. A method of analyzing composition or structure of a thin film or layer by measuring a depth dependent profile of at least one of absorption, photoluminescence, secondary chemi-luminescence, black-body emission and scattering of radiation in the thin film or layer, the method comprising:

providing a suitable test material having a depth axis extending through a thin film or layer, said test material being provided with a substantially flat image transfer surface having an orientation substantially parallel to and in proximity to said depth axis;

projecting a beam from a source of radiation into said test material along said depth axis thereby causing emission of radiation from said test material through said image transfer surface; and collecting at least part of said emission of radiation transmitted through said image transfer surface to form an image of a depth dependent profile of at least a part of said thin film or layer.

2. The method as defined in claim 1, wherein said beam of radiation is a collimated beam.

3. The method as defined in claim 1, wherein said beam comprises light, and said image is recorded for a plurality of wavelengths, whereby said analyzing comprises using wavelength sensitivity to light of said thin film or layer to provide information for determining said composition or structure.

4. The method as defined in claim 2, wherein said beam comprises light, and said image is recorded for a plurality of wavelengths, whereby said analyzing comprises using wavelength sensitivity to light of said thin film or layer to provide information for determining said composition or structure.

5. The method as defined in claim 2, wherein said beam comprises light, and said step of collecting comprises:

aligning an imaging system with its principal axis oriented perpendicular to said image transfer surface, and aligning said imaging system so that said principal axis intersects a volume of said test material irradiated by said beam;

focusing said imaging system so as to form an image of said irradiated volume, from radiation emitted therefrom and transmitted through said image transfer surface of said test material; and recording said image formed by said imaging system using a camera or image recording device.

6. The method as defined in claim 2, wherein said beam comprises light, and said step of projecting comprises:

splitting said beam into forward and reverse beams using a beam splitter element;

steering said forward and reverse beams so as to propagate along separate paths using a set of beam steering elements so as to propagate through said test material from opposing directions; and projecting said forward beam into said test material, and projecting said reverse beam into said test material, consecutively and non-coincidently in time, through the use of beam shattering devices which consecutively and non-coincidently in time permit the intersection of each of said forward and reverse beams with said test material thereby causing a volume of said test material intersected by said forward beam and a volume of said test material intersected by said reverse beam.

7. The method as defined in claim 6, wherein said forward and reverse beams propagate along said depth axis and intersect a same said volume.

8. The method as defined in claim 7, wherein said collecting comprises:

recording the images formed of said irradiated volumes of said test material using a camera or image recording device;

converting the data from said images transmitted by said camera into a format for mathematical processing; and storing said formatted image data in a memory of data processing device, wherein said stored formatted image data is processed to separately resolve an image arising from the attenuation depth profile contrast from that arising from matrix contrast.

9. The method as defined in claim 6, wherein said collecting comprises:

recording the images formed of said irradiated volumes of said test material using a camera or image recording device;

converting the data from said images transmitted by said camera into a format for mathematical processing; and storing said formatted image data in a memory of data processing device, wherein said stored formatted image data is processed to separately resolve an image arising from the attenuation depth profile contrast from that arising from matrix contrast.

10. The method as defined in claim 2, wherein said step of collecting comprises forming said image by accepting light from a volume near said depth axis and rejecting light outside of said volume.

11. The method as defined in claim 4, wherein said step of collecting comprises forming said image by accepting light from a volume near said depth axis and rejecting light outside of said volume.

12. The method as defined in claim 6, wherein said step of collecting comprises forming said image by accepting light from a volume near said depth axis and rejecting light outside of said volume.

* * * * *